(12) United States Patent
Shang

(10) Patent No.: US 11,058,511 B1
(45) Date of Patent: Jul. 13, 2021

(54) MEDICAL OPTICAL FIBER GUIDEWIRE CONVERTER

(71) Applicant: Hua Shang, Nanjing (CN)

(72) Inventor: Hua Shang, Nanjing (CN)

(*) Notice: Subject to any disclaimer, the term of this patent is extended or adjusted under 35 U.S.C. 154(b) by 0 days.

(21) Appl. No.: 17/184,389

(22) Filed: Feb. 24, 2021

Related U.S. Application Data

(63) Continuation of application No. PCT/CN2020/089532, filed on May 11, 2020.

(30) Foreign Application Priority Data

Feb. 25, 2020 (CN) .......................... 202010114497.5

(51) Int. Cl.
  *G02B 6/44* (2006.01)
  *A61B 90/30* (2016.01)
  *A61B 90/13* (2016.01)

(52) U.S. Cl.
  CPC .............. *A61B 90/30* (2016.02); *A61B 90/13* (2016.02); *G02B 6/4401* (2013.01); *G02B 6/4439* (2013.01); *A61B 2090/306* (2016.02)

(58) Field of Classification Search
  CPC .. G02B 6/4401; G02B 6/4439; G02B 6/4436; A61B 90/30; A61B 90/13
  See application file for complete search history.

(56) References Cited

U.S. PATENT DOCUMENTS 6,409,391 B1    6/2002  Chang
10,101,550 B1 * 10/2018  Hsia ..................... G02B 6/4436

FOREIGN PATENT DOCUMENTS

| | | |
|---|---|---|
| CN | 1344377 A | 4/2002 |
| CN | 102902028 A | 1/2013 |
| CN | 203465448 U | 3/2014 |
| CN | 206960724 U | 2/2018 |
| CN | 108398753 A | 8/2018 |
| JP | 2019095783 A | 6/2019 |

OTHER PUBLICATIONS

International Search Report dated Oct. 27, 2020; International Application No. PCT/CN2020/089532; 5 pgs.; ISA/CN, Beijing, Republic of China.

* cited by examiner

*Primary Examiner* — Sung H Pak
*Assistant Examiner* — Hoang Q Tran
(74) *Attorney, Agent, or Firm* — Andrew D. Fortney; Central California IP Group, P.C.

(57) ABSTRACT

A medical optical fiber guidewire converter includes a first connector; a second connector; a conversing optical fiber with an overcurrent channel configured to transmit laser light and including a first and second optical fibers and a connecting optical fiber, a diameter of the first optical fiber is greater than that of the second optical fiber, the first optical fiber is connected to the first connector, and the second optical fiber is connected to the second connector; and a heat sink on the conversing optical fiber. The medical optical fiber guidewire converter couples optical fiber guidewires with different core diameters using the connecting optical fiber, thereby ensuring safety and reliability of laser light transmission in the overcurrent channel. The heat sink can absorb laser light overflowing from the conversing optical fiber and dissipate heat therefrom to reduce the temperature of and avoid thermal damage to the conversing optical fiber.

8 Claims, 4 Drawing Sheets

MEDICAL OPTICAL FIBER GUIDEWIRE CONVERTER

CROSS REFERENCE TO RELATED APPLICATIONS

The present application is a continuation of International Application No. PCT/CN2020/089532, filed May 11, 2020, which claims priority to Chinese Pat. Appl. No. 202010114497.5, filed on Feb. 25, 2020, each of which is incorporated herein by reference.

TECHNICAL FIELD

The disclosure relates to the technical field of medical optical fiber guidewires, in particular to a medical optical fiber guidewire converter.

BACKGROUND

At present, Seldinger arterial intubation technique is very mature. Under the guidance of clinical imaging medicine (X-ray, CT, MR, B-us, etc.), a delicate instrument, such as a special catheter or guidewire is inserted into the lesion via percutaneous vascular route or an original channel in human body, so as to achieve a diagnostic imaging and treatment.

However, in the process of photodynamic therapy, it is necessary to connect a laser with a specific wavelength (for example, 630 nm, 650 nm, etc.) to an optical fiber guidewire. Optical fiber guidewires have different specifications, so as to match different lesions. In the practices, it is required to connect output fibers of the laser which have different core diameters to the optical fiber guidewires. Therefore, a converter that can couple fiber guidewires having different core diameters is required.

Therefore, it is necessary to develop a medical optical fiber guidewire converter, so as to solve the above technical problems.

SUMMARY

An object of the disclosure is to provide a medical optical fiber guidewire converter to couple the optical fiber guidewires having different core diameters, ensuring the safety and reliability of laser light transmission during treatment.

The above object of the disclosure can be achieved by following technical solutions.

The disclosure provides a medical optical fiber guidewire converter. The medical optical fiber guidewire converter includes a first connector and a second connector. The first connector is used to connect with one of a laser and an optical fiber guidewire, and the second connector is used to connect with the other one of the laser and the optical fiber guidewires.

The medical optical fiber guidewire converter also includes a conversing optical fiber with an overcurrent channel for transmitting laser is formed inside. The conversing optical fiber includes a first optical fiber, a second optical fiber, and a connecting optical fiber connected with the first optical fiber and the second optical fiber. A diameter of the first optical fiber is greater than a diameter of the second optical fiber. The first optical fiber is connected to the first connector, and the second optical fiber is connected to the second connector. The medical optical fiber guidewire converter also includes a heat sink provided on the conversing optical fibers. The heat sink is used to absorb laser light overflowing from the conversing optical fiber to reduce a temperature of the conversing optical fiber.

In some examples of the disclosure, a diameter of the connecting optical fiber gradually decreases along a length direction of the connecting optical fiber. An end of the connecting optical fiber with a larger diameter is connected to the first optical fiber, and an end of the connecting optical fiber with a smaller diameter is connected to the second optical fiber.

In some examples of the disclosure, the heat sink is made by a transparent material and is arranged around the conversing optical fiber.

In some examples of the disclosure, an outer surface of the heat sink is provided with a coating, and the coating is used to absorb heat of the laser light.

In some examples of the disclosure, a refractive cavity is formed in the heat sink, and the laser light is repeatedly refracted in the refractive cavity.

In some examples of the disclosure, the heat sink is arranged in the form of a plurality of heat sinks arranged at intervals along a length direction of the conversing optical fibers.

In some examples of the disclosure, the heat sink is tapered. An inward inclination angle between the heat sink and an axis of the conversing optical fiber is 30 degrees, and a camber angle between the heat sink and the axis of the conversing optical fiber is 60 degrees.

In some examples of the disclosure, the conversing optical fiber includes a core fiber, a cladding layer, and a polymer cladding layer that are successively arranged from inside to outside. The core fiber delimits the overcurrent channel, and has a refractive index higher than a refractive index of the cladding layer.

In some examples of the disclosure, a numerical aperture of the conversing optical fiber is calculated by formula $N.A = \sqrt{n_1 - n_2}$, where $n_1$ represents the refractive index of the core fiber, and $n_2$ represents the refractive index of the cladding layer.

In some examples of the disclosure, a numerical aperture of the first optical fiber is 0.37, and a numerical aperture of the second optical fiber is 0.22.

The medical optical fiber guidewire converter of the disclosure has the following features and advantages. By using the connecting optical fibers to connect the first optical fiber and the second optical fiber with different diameters, the coupling of the optical fiber guidewires with different core diameters is realized, thereby ensuring the safety and reliability of laser light transmission in the overcurrent channel during the treatment.

Meanwhile, the heat sink provided on the conversing optical fiber can absorb the laser light overflowing from the conversing optical fiber and dissipate heat therefrom, so as to reduce the temperature of the conversing optical fiber and avoid the thermal damage of the conversing optical fiber.

BRIEF DESCRIPTION OF THE DRAWINGS

In order to illustrate the technical solutions in the embodiments of the disclosure more clearly, the disclosure will be further elaborated with the drawings for illustrating the embodiments. It is apparent that the drawings illustrated below only show some embodiments of the disclosure. Other drawings may further be obtained by those of ordinary skill in the art according to these drawings without creative work.

Figure 1:
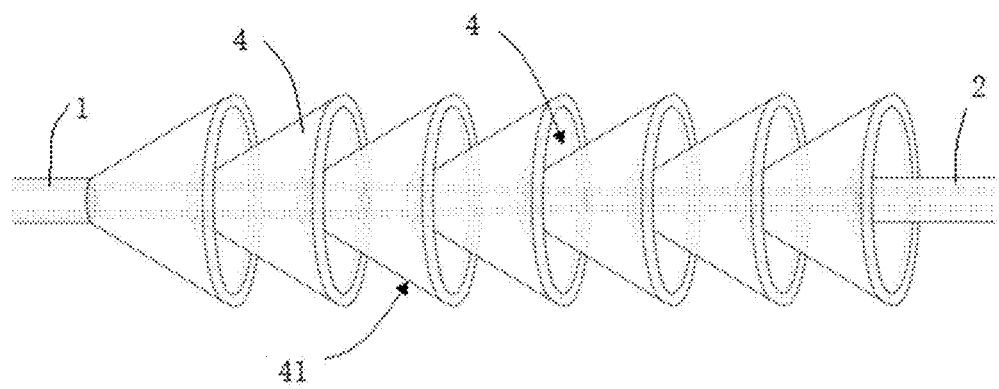
FIG. 1 is a three-dimensional schematic diagram of a medical optical fiber guidewire converter according to an example of the disclosure.

LIST OF REFERENCE SYMBOLS 1, first connector;
2, second connector;
3, conversing optical fiber; 31, first optical fiber; 32, second optical fiber; 33, connecting optical fiber; 34, overcurrent channel;
4. heat sink; 41, coating; 42, refraction cavity.

DETAILED DESCRIPTION

The embodiments of the disclosure are described below in detail in combination with reference to the drawings. Throughout the disclosure, the same or similar reference symbols indicate the same or similar elements or elements with the same or similar functions. The embodiments described below with reference to the drawings are exemplary, are merely used to illustrate the disclosure, but are not intended to limit the disclosure.

In the disclosure, it should be understood that terms "center", "longitudinal", "transverse", "length", "width", "thickness", "upper", "lower", "front", "back", "left", "right", "vertical", "horizontal", "top", "bottom", "inner", "outer", "clockwise", "counterclockwise", "axial", "radial", "circumferential" and the like indicating the directional or positional relationship are based on the directional or positional relationship shown in the accompanying drawings. These terms are used for purposes of convenience and clarity only, rather than indicating or implying that the discussed device or element must have a specific orientation, or must be constructed and operated in the specific orientation. Therefore, these terms should not be construed to limit the scope of the disclosure. In addition, the features defined with "first" and "second" may explicitly or implicitly include one or more of these features. In the description, unless otherwise specified, the term "a plurality of" means "two or more".

In the description of the disclosure, unless otherwise clearly specified and limited, the terms "installation", "connected" and "connection" should be understood in a broad sense, for example, indicating a fixed connection, detachable connection or integral connection; a mechanical connection or an electrical connection; direct connection or indirect connection through an intermediate element; or an internal communication between two components. For those of ordinary skill in the art, they can determine the specific meaning of the above-mentioned terms in the disclosure according to the specific situations.

Example 1

As shown in FIGS. 1-4, the disclosure provides a medical optical fiber guidewire converter. The medical optical fiber guidewire converter includes a first connector 1 and a second connector 2. The first connector 1 is used to connect with one of a laser and an optical fiber guidewire, and the second connector 2 is used to connect with the other one of the laser and the optical fiber guide wire.

The medical optical fiber guidewire converter also includes a conversing optical fiber 3 with an overcurrent channel 34 for transmitting lase light is formed inside. The conversing optical fiber 3 includes a first optical fiber 31, a second optical fiber 32, and a connecting optical fiber 33 connected with the first optical fiber 31 and the second optical fiber 32. A diameter of the first optical fiber 31 is greater than a diameter of the second optical fiber 32. The first optical fiber 31 is connected to the first connector 1, and the second optical fiber 32 is connected to the second connector 2. The medical optical fiber guidewire converter also includes a heat sink 4 provided on the conversing optical fibers 3. The heat sink 4 is used to absorb laser light overflowing from the conversing optical fibers 3 to reduce a temperature of the conversing optical fibers 3.

It should be noted that the optical fiber guidewire has a diameter similar to an ordinary guidewire, but is a special function guidewire that can transmit laser light inside. After connecting with the laser, the optical fiber guidewire enters into a blood vessel via a percutaneous route through the Seldinger arterial intubation technique and then into the human organs, such as the liver and kidney, through the blood vessel, so as to treat solid tumors inside the human organs. Compared with conventional treatments such as surgery, chemotherapy and radiotherapy, photodynamic therapy has several advantages including small trauma, low toxicity, good targeting and good applicability. After the laser light is introduced into the tumor through the optical fiber guidewire, this therapy overcomes the difficulty of exposing the lesion to the external laser light by illuminating body surface or by surgical, thereby improving the efficacy and reducing complications of photodynamic therapy.

Seldinger arterial intubation technique is very mature. Under the guidance of clinical imaging medicine (X-ray, CT, MR, B-us, etc.), a delicate instrument, such as a special catheter or guidewire is inserted into the lesion via percutaneous vascular route or an original channel in human body, so as to achieve a diagnostic imaging and treatment. This technique uses the metal guidewire via percutaneous vascular route to enter the blood vessel and reach the lesion. This method is simple in operation, slight in damage, and does not need to suture the blood vessels. Thus, it completely replaces previous methods which need to cut open the blood vessels surgically, and becomes a basic operation technique of modern interventional radiology. This method has achieved good effects in tumor thrombosis and drug perfusion, intra-arterial irradiation, prevention of radiation damage, chemotherapy, preoperative embolization of tumor blood vessels, vasoactive drugs and alcohol perfusion, etc.

In the medical optical fiber guidewire converter of the disclosure, the connecting optical fiber 33 is used to connect the first optical fiber 31 and the second optical fiber 32 with different diameters, so as to realize the coupling of the optical fiber guidewires with different core diameters, thereby ensuring the safety and reliability of laser transmission in the overcurrent channel 34 during the treatment.

Since the first optical fiber 31 differs from the second optical fiber 32 in the diameter and numerical aperture, the laser light will overflow from the conversing optical fiber 3 when entering into the optical fiber having the smaller numerical aperture from the optical fiber having the larger numerical aperture, causing energy loss and heating effect on the connector and the outer structure of the optical fiber. By providing a heat sink 4 on the conversing optical fiber 3, the laser light overflowing from the conversion fiber 3 can be absorbed by the heat sink 4 and the heat can also be dissipated. Therefore, the temperature of the conversing optical fiber 3 is reduced, avoiding the thermal damage of the conversing optical fiber 3.

In some examples of the disclosure, a diameter of the connecting optical fiber 33 gradually decreases along a length direction of the connecting optical fiber 33. An end of the connecting optical fiber 33 with a larger diameter is connected to the first optical fiber 31, and an end of the connecting optical fiber 33 with a smaller diameter is connected to the second optical fiber 32. It can be understood that the connecting optical fiber 33 is tapered, so as to facilitate connecting the first optical fiber 31 and the second optical fiber 32.

In some examples of the disclosure, the first connector 1 and the second connector 2 may be common optical fiber connectors, such as SMA905, FC-PC connector. Alternatively, they may be customized connectors in other forms. In this example, the first connector 1 is connected to the laser, and the second connector 2 is connected to the optical fiber guidewire. Because the output fiber of the laser has a diameter larger than the diameter of the optical fiber guidewire, the laser light is transmitted from the first optical fiber 31 (an optical fiber with a larger diameter) to the second optical fiber 32 (an optical fiber with a smaller diameter).

Figure 4:
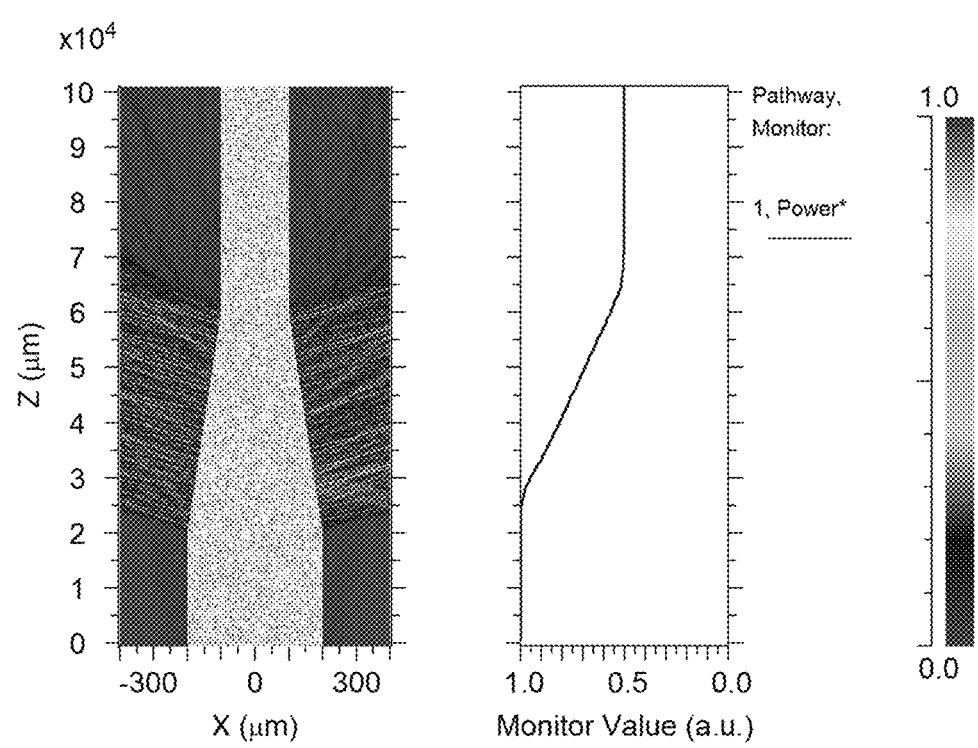
FIG. 4 is a schematic diagram of energy loss when laser light is transmitted from the first optical fiber to the second optical fiber according to an example of the disclosure.

It can be understood that when the lengths of the first optical fiber 31 and the second optical fiber 32 are both 6 mm, the length of the connecting optical fiber 33 is 4 mm, the connecting optical fiber 33 has a core diameter of 400 μm at one end and a core diameter of 200 μm at the other end. FIG. 4 shows that the transmission of the laser light from the optical fiber with a larger diameter to the optical fiber with a smaller diameter when the laser light transmitted has a wavelength of 650 nm. From the right figure of FIG. 4, it can be seen that the laser light overflows from sides of the connecting optical fiber 33, resulting in loss of laser light. From the left figure of FIG. 4, it can be seen that the laser light overflowing from the connecting optical fiber 33 gradually increases with the increase of the transmission distance, and finally about 50% of the laser light enter into the second optical fiber 32. The loss of the laser light mainly occurs at the tapered fiber portion of the connecting optical fiber 33.

In some examples of the disclosure, the heat sink 4 is tapered. An inward inclination angle between the heat sink 4 and an axis of the conversing optical fiber 3 is 30 degrees, and a camber angle between the heat sink 4 and the conversing optical fiber 3 is 60 degrees. A conical structure with an inclination angle is arranged outside the connecting optical fiber 33, and has an outer diameter of 4 mm, a camber angle of 30 degrees, and an inward inclination angle of 60 degrees. Through this structure, the overflowing laser light can be better consumed.

In some examples of the disclosure, the heat sink 4 is made by a transparent material. The heat sink 4 is arranged around the conversing optical fiber 3. The heat sink 4 may be made by quartz, glass, polymer (such as polystyrene, polymethyl methacrylate, polycarbonate, fluoroplastics) to transmit the overflowing laser light.

In some examples of the disclosure, an outer surface of the heat sink 4 is provided with a coating 41, and the coating 41 is used to absorb heat of the laser light. The coating 41 may be a metal film or a metal coating 41 (such as aluminum, zinc, copper, steel) that is plated on the surface of the heat sink 4, and then oxidized to black by anodizing. As a result, the laser light overflowing from the conversing optical fiber 3 is repeatedly reflected and absorbed in the conical heat sink 4. In addition, by increasing the heat dissipation area of the heat sink 4, heat is finally dissipated into the space through natural convection of air.

When the incident power is 200 mW and the power loss is 100 mW, the laser light power of 100 mW is converted into heat and then dissipated by metal coating 41 on the surface. Through the natural convection cooling of the air, the temperature outside the converter of the disclosure is about 48° C., which will not cause damage to the optical fiber structure. In the case that higher transmission power is required, the diameter of the conical heat sink 4 can be appropriately increased to increase the heat dissipation area of the heat sink 4, which will cause the further reduction of the temperature.

In some examples of the disclosure, a refraction cavity 42 is formed in each conical heat sink 4, and the laser light is repeatedly refracted in the refraction cavity 42, greatly increasing the heat dissipation efficiency. In some examples of the disclosure, there are a plurality of heat sinks 4, and the plurality of the heat sinks 4 are arranged at intervals along the length direction of the conversing optical fibers 3.

In some examples of the disclosure, the conversing optical fiber 3 includes a core fiber, a cladding layer, and a polymer cladding layer that are successively arranged from inside to outside. The core fiber delimits the overcurrent channel 34, and has a refractive index higher than a refractive index of the cladding layer. It can be understood that the conversing optical fiber 3 has a core fiber, a cladding layer and a polymer cladding layer. The core fiber is mixed with the cladding layer through doping and other means, and the refractive index of the core fiber is higher than that of the cladding layer, so that the laser light is confined to transmit inside the core fiber. The main function of the polymer cladding layer is to protect the cladding layer and strengthen the mechanical strength of the optical fiber. The connecting optical fiber 33 is formed by tapering an optical fiber with a larger diameter. The diameters of core fiber and cladding lager are varied linearly, and the laser light is confined to be transmitted in the tapered structure of the core.

Figure 2:
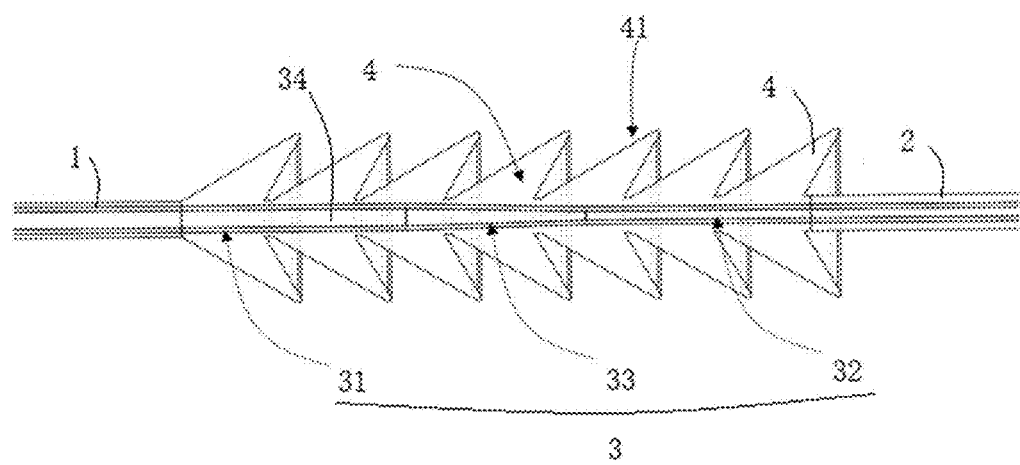
FIG. 2 is a schematic diagram of a medical optical fiber guide wire converter according to an example of the disclosure.
Figure 3:
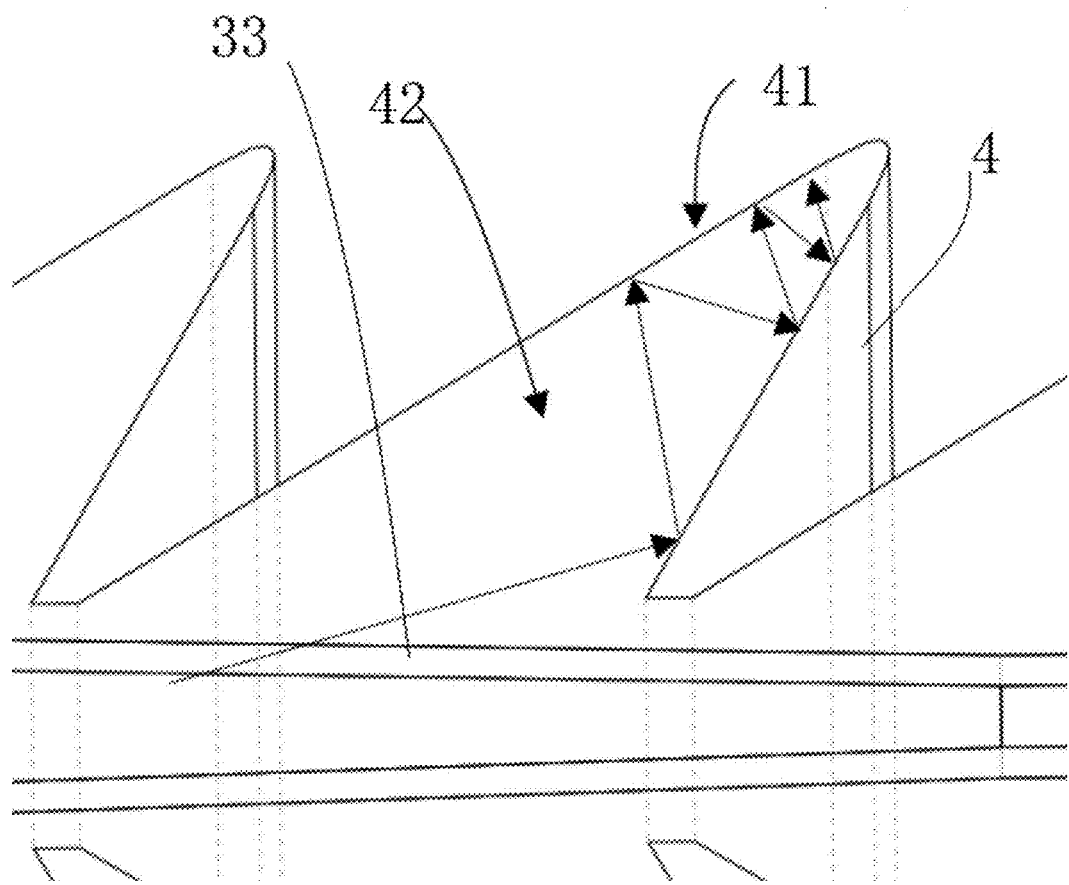
FIG. 3 is a partial schematic diagram of a conversing optical fiber according to an example of the disclosure.

In some examples of the disclosure, generally, there are a plurality of heat sinks. These conical heat sinks are sleeved together end to end, and the smaller diameter portion of the heat sink at the front is located in the conical cavity of the following conical heat sink. In addition, the wall of each conical heat sink forms the refraction cavity 42 through the inner side wall and the outer side wall, as shown in FIGS. 2-3.

Example 2

Figure 5:
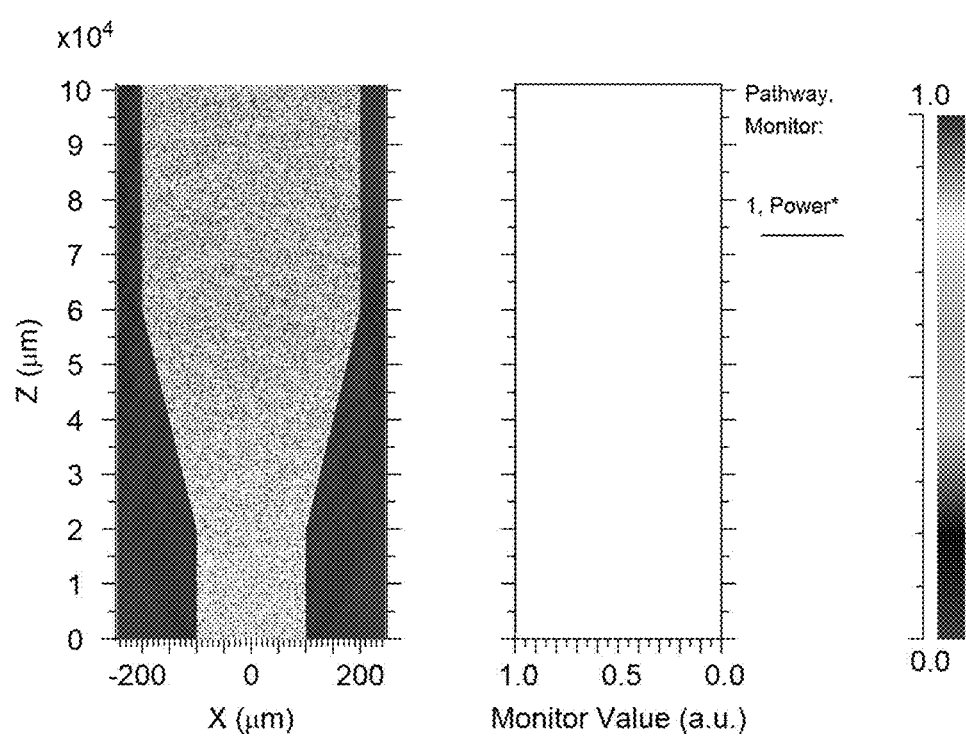
FIG. 5 is a schematic diagram of energy loss when laser light is transmitted from the second optical fiber to the first optical fiber according to an example of the disclosure.

As shown in FIG. 5, the difference between this example and example 1 is that the first connector 1 is connected to the optical fiber guidewire 33, and the second connector 2 is connected to the laser, so that the laser light is transmitted from the second optical fiber 32 (an optical fiber with a smaller diameter) to the first An optical fiber 31 (an optical fiber with a larger diameter).

It can be understood that the length of the first optical fiber 31 and the second optical fiber 32 are both 6 mm, the length of the connecting optical fiber 33 is 4 mm, and the connecting optical fiber 33 has a core diameter of 400 μm at one end and a core diameter of 200 μm at the other end. FIG. 5 shows that the transmission of the laser light from the optical fiber with a smaller diameter to the optical fiber with a larger diameter when the laser light transmitted has a wavelength of 650 nm. From the left figure of FIG. 5, a tapered fiber section can be seen, and the laser light is transmitted from bottom to top. The right figure of FIG. 5 shows that the power attenuation of laser light transmission in the tapered optical fiber, and the input power is normalized power as 1. At this time, there is basically no loss of the laser, and thus about 100% of the laser energy is coupled into the optical fiber with the larger diameter.

Example 3

The difference between this example and the above examples lies in the follows.

In this example, a numerical aperture of the converging optical fiber 3 is calculated by formula $N.A=\sqrt{n_1-n_2}$, where $n_1$ represents the refractive index of the core fiber, and $n_2$ represents the refractive index of the cladding layer. In some examples of the disclosure, the numerical aperture of the first optical fiber 31 is 0.37, and the numerical aperture of the second optical fiber 32 is 0.22.

When the output fiber of the laser has a core diameter of 400 μm, the core wire of the optical fiber guidewire has a diameter of 200 μm. The output interface of the laser is an SMA905 connector, the input interface of the optical fiber guidewire is an SMA905 connector, the numerical aperture (N.A) of the multimode optical fiber of the laser is 0.37, and the numerical aperture (N.A) of the multimode optical fiber of the optical fiber guidewire is 0.22. According to the above formula, the difference between the refractive index (n1−n2) in the first optical fiber 31 is selected as 0.05, so that the numerical aperture (N.A) of the first optical fiber 31 is 0.37, and the loss is minimized when the first optical fiber 31 is connected to the laser. Meanwhile, upon the calculation in the same way, the numerical aperture of the second optical fiber 32 is 0.22, so that the loss is minimized when the second optical fiber 32 is connected to the optical fiber guidewire.

In the description, the illustration with reference to the terms "one embodiment", "some embodiments", "exemplary embodiments", "example", "specific example", or "some examples" and the like means that the specific features, structures, materials or characteristics described in combination with the embodiment or example are included in at least one embodiment or example of the disclosure. In the present description, the schematic representation of the above-mentioned terms does not necessarily refer to the same embodiment or example. Moreover, the specific features, structures, materials or characteristics illustrated thereby may be combined in any one or more embodiments or examples in a suitable manner.

Although embodiments of the present disclosure have been shown and described, it should be appreciated for those skilled in the art that various modifications, changes, replacements and variants may be made to these embodiments without departing from the principle and purpose of the present disclosure, and the scope of the disclosure is defined by the claims and their equivalents.

The invention claimed is:

1. A medical optical fiber guidewire converter, comprising:
    a first connector configured to connect with one of a laser and an optical fiber guidewire, and a second connector configured to connect with the other one of the laser and the optical fiber guidewire;
    a conversing optical fiber with an overcurrent channel configured to transmit laser light, wherein the conversing optical fiber comprises a first optical fiber, a second optical fiber, and a connecting optical fiber connected with the first optical fiber and the second optical fiber, a diameter of the first optical fiber is greater than a diameter of the second optical fiber, the first optical fiber is connected to the first connector, and the second optical fiber is connected to the second connector;
    a tapered heat sink around the conversing optical fiber and comprising a transparent material, configured to absorb laser light overflowing from the conversing optical fiber to reduce a temperature of the conversing optical fiber, wherein an inward inclination angle between the heat sink and an axis of the conversing optical fiber is 30 degrees, and a camber angle between the heat sink and the axis of the conversing optical fiber is 60 degrees.

2. The medical optical fiber guidewire converter according to claim 1, wherein a diameter of the connecting optical fiber gradually decreases along a length direction of the connecting optical fiber, an end of the connecting optical fiber with a larger diameter is connected to the first optical fiber, and an end of the connecting optical fiber with a smaller diameter is connected to the second optical fiber.

3. The medical optical fiber guidewire converter according to claim 1, wherein an outer surface of the heat sink includes a coating, and the coating absorbs heat of the laser light.

4. The medical optical fiber guidewire converter according to claim 1, wherein a refractive cavity is in the heat sink, and the laser light is repeatedly refracted in the refractive cavity.

5. The medical optical fiber guidewire converter according to claim 1, wherein the heat sink comprises a plurality of heat sinks at intervals along a length direction of the conversing optical fibers.

6. The medical optical fiber guidewire converter according to claim 1, wherein the conversing optical fiber comprises a core fiber, a cladding layer, and a polymer cladding layer successively from inside to outside,
    the core fiber delimits the overcurrent channel and has a refractive index higher than a refractive index of the cladding layer.

7. The medical optical fiber guidewire converter according to claim 6, wherein a numerical aperture of the conversing optical fiber is calculated by a formula $N.A=\sqrt{n_1-n_2}$, wherein $n_1$ represents the refractive index of the core fiber, and $n_2$ represents the refractive index of the cladding layer.

8. The medical optical fiber guidewire converter according to claim 7, wherein the numerical aperture of the first optical fiber is 0.37, and the numerical aperture of the second optical fiber is 0.22.

* * * * *